(12) United States Patent
Theisinger et al.

(10) Patent No.: US 8,796,340 B2
(45) Date of Patent: Aug. 5, 2014

(54) PHARMACEUTICAL COMPOSITION COMPRISING PROPOFOL

(75) Inventors: Bastian Theisinger, Mannheim (DE); Sonja Theisinger, Mannheim (DE)

(73) Assignee: Novaliq GmbH, Heidelberg (DE)

( * ) Notice: Subject to any disclaimer, the term of this patent is extended or adjusted under 35 U.S.C. 154(b) by 9 days.

(21) Appl. No.: 13/511,184

(22) PCT Filed: Nov. 22, 2010

(86) PCT No.: PCT/EP2010/067938
§ 371 (c)(1),
(2), (4) Date: May 22, 2012

(87) PCT Pub. No.: WO2011/061332
PCT Pub. Date: May 26, 2011

(65) Prior Publication Data
US 2012/0238639 A1   Sep. 20, 2012

(30) Foreign Application Priority Data

Nov. 23, 2009  (EP) .................................... 09014548

(51) Int. Cl.
*A61K 31/05*   (2006.01)

(52) U.S. Cl.
USPC .......................................................... 514/731

(58) Field of Classification Search
USPC .......................................................... 514/731
See application file for complete search history.

(56) References Cited

U.S. PATENT DOCUMENTS 5,496,537 A   3/1996  Henry
6,262,126 B1  7/2001  Meinert

FOREIGN PATENT DOCUMENTS

WO         0054588 A1    9/2000

*Primary Examiner* — Raymond Henley, III
(74) *Attorney, Agent, or Firm* — Dennemeyer & Associates, LLC.

(57) ABSTRACT

The invention provides novel pharmaceutical compositions comprising the active ingredient propofol. Preferably, propofol is dissolved in at least one semifluorinated alkane. The compositions, which are preferably liquid or gel-like, may optionally comprise further excipients. They may be used as fill material in capsules, as buccal or nasal sprays, or as aerosols for pulmonary administration. They are particularly useful for the transmucosal administration of propofol.

17 Claims, No Drawings

PHARMACEUTICAL COMPOSITION COMPRISING PROPOFOL

BACKGROUND

Propofol (2,6-diisopropylphenol, MW 178.27) is a pharmacologically active compound known as a potent intravenous anaesthetic. It is routinely used for both the induction and the maintenance of anaesthesia. It is characterised by its rapid onset of action and its relatively mild side effects.

Physically, propofol is a highly lipophilic compound which melts at about 19° C. At room temperature, it has the appearance of an oil. Its solubility in water or aqueous buffers is negligible, which makes propofol a highly challenging compound to formulate, in particular for intravenous administration, but also for other routes. The only ionisable group of the molecule is its hydroxyl group, which is however unsuitable for forming a water soluble salt due to its $pK_a$ of 11. The octanol/water partition coefficient for propofol is 6761:1 at a pH of 6-8.5.

Propofol was first developed by the British pharmaceutical company ICI (now AstraZeneca) as a solubilised intravenous formulation which contained substantial amounts of the solubiliser Cremophor® EL, an excipient which is not very well tolerated. Shortly after the market introduction, several reports of anaphylactic reactions led to the withdrawal of the formulation. Several years later, AstraZeneca launched a new formulation of propofol branded as Diprivan® which is still used today. This product is an o/w-emulsion comprising 1% of propofol and 10% of soy bean oil as the dispersed phase and 1.2% purified egg lecithin as emulsifier. The coherent aqueous phase contains 2.25% of glycerol and small amounts of EDTA and sodium hydroxide. In recent years, generic emulsion formulations have also become available in a number of countries.

Propofol is indicated for the induction and maintenance of general anaesthesia, sedation for mechanically ventilated adults, and procedural sedation. Other clinical uses which are still experimental include for the management of status epilepticus, the treatment of headache, in particular migraine headache, the management of anxiety, and neuroprotection in acute brain injury. These uses often require only sub-hypnotic doses of propofol, as taught, for example, in WO 00/54588 A1.

Compared to other compounds used in anaesthesia, propofol has a remarkable safety profile. Its adverse effects are usually mild and easily managed. The hypnotic effect of a single dose of propofol typically wears off within minutes. The rapid onset and recovery along with its amnestic effects have made the compound very popular for sedation and anaesthesia. In contrast to similar agents, it does not appear to induce nausea.

Among the typical adverse effects are a lowered blood pressure and transient apnoea following induction doses. Mild myoclonic movements are commonly observed. Another frequent issue of the propofol emulsion is that it produces local pain at the site of injection or infusion, for which reason some patients are pre-treated with a local anaesthetic such as lidocaine. It is believed that the small fraction of propofol dissolved in the aqueous phase of the emulsion is responsible for this pain. Rare but more serious are dystonia, hyperlipidaemia, pancreatitis and the so-called propofol infusion syndrome. This potentially lethal metabolic derangement has occurred in critically ill patients after a prolonged infusion of high-dose propofol in combination with catecholamines and/or corticosteroids.

More recently, other intravenous formulations of propofol have been tested clinically or introduced to the market. For example, a 1% propofol emulsion with only 5% of soybean oil and 0.6% lecithin (Ampofol®) has been studied. It is likely that this formulation may be associated with a lower risk of hyperlipidaemia and pancreatitis. At the same time, the pain at the injection site was found to be even more pronounced than with Diprivan®.

Other formulations such as Propofol-Lipuro® and IDD-D® propofol rely on a higher fraction of medium chain triglycerides (MCT) to replace long chain triglycerides (LCT) in the oil component of the emulsion. It is assumed that MCT's are better tolerated than LCT's by both adults and paediatric patients. However, they may also release toxic compounds such as acetoacetate, beta-hydroxybutyrate and octanoates.

Non-emulsion formulations which have been suggested for propofol include aqueous solutions in which the drug substance is present in solubilised form with the aid of a cyclodextrin. Cyclodextrins are water-soluble cyclic oligosaccharides capable of forming inclusion complexes with guest molecules. In particular, propofol solutions with hydroxypropyl-β-cyclodextrin and with sulphobutylether-β-cyclodextrin, respectively, have been studied. However, it has not been established whether the pharmacokinetics of these formulations is comparable to the propofol emulsions. Moreover, high doses of cyclodextrins are often linked with haemolytic effects and renal toxicity.

U.S. Pat. No. 5,496,537 describes aerosol formulations of propofol comprising hydrofluorocarbon propellants. However, the inhalation of propellant-driven formulations is not easy for paediatric or elderly patients who may not be able to perform the required breathing manoeuvre. Moreover, the pulmonary tolerability of propofol has not been established.

Therefore, there is a need for further improvements in propofol formulations. For example, there is a need for formulations which do not cause carrier-related toxic effects such as hyperlipidaemia or haemolysis. Moreover, there is a need for formulations and methods which allow the administration of propofol in a convenient, flexible, and pain-free manner.

It is therefore an object of the present invention to provide propofol formulation which do not possess one or more of the disadvantages of the presently known formulations. Another object is to provide methods for administering propofol in a safe, tolerable and patient-friendly manner. Further objects will become apparent on the basis of the description and the patent claims.

SUMMARY OF THE INVENTION

In a first aspect, the invention provides a pharmaceutical composition comprising a therapeutically effective amount of propofol and a semifluorinated alkane. The composition is typically a liquid formulation or a gel. In a preferred embodiment, propofol is dissolved in the semifluorinated alkane. The concentration of propofol in the composition may be 1 wt.-% or higher, such as wt.-% or more.

In a further aspect, the invention provides uses of propofol compositions based on semifluorinated alkanes. In a particular embodiment, the compositions are administered topically, such as to the oral or nasal mucosa, or by inhalation. Clinically, they may be used for inducing or maintaining sedation or anaesthesia. Further therapeutic uses include the prevention or treatment of headaches, such as migraine headache, the prevention or treatment of nausea, such as chemotherapy-induced nausea, the management of status epilepticus, anxiety disorders, or to provide neuroprotection in brain trauma.

In a further aspect, the invention provides pharmaceutical dosage forms comprising such propofol compositions, such as soft capsules, oral sprays, oral gels, oral liquids, nasal sprays, or inhalable aerosols in the form of metered dose inhalers or nebuliser solutions, as well as packages, containers or kits comprising the compositions.

Yet further aspects of the invention will be apparent from the detailed description below.

DETAILED DESCRIPTION OF THE INVENTION

According to a first aspect of the invention, a pharmaceutical composition is provided which comprises a therapeutically effective amount of propofol and a semifluorinated alkane.

As used herein, a pharmaceutical composition is a composition comprising at least one pharmacologically active ingredient or diagnostic agent in combination with at least one pharmaceutical excipient.

Propofol means the pharmacologically active compound 2,6-di(propan-2-yl)phenol (CAS no. 2078-54-8), or any of its salts, solvates, complexes, conjugates and derivatives. Preferably, the invention is carried out with underivatised propofol in its free form, as it is also present in the currently available drug products of propofol, such as Diprivan®.

A therapeutically effective amount refers to a dose, concentration or strength which is useful for producing a desired pharmacological effect. Depending on the patient (e.g. adult or paediatric, healthy or ill) and on the type of effect that is desired (e.g. whether sedation, anaesthesia, or control of headache), the therapeutically effective amount of propofol may differ substantially.

Semifluorinated alkanes are linear or branched alkanes some of whose hydrogen atoms have been replaced by fluorine. In a preferred embodiment, the semifluorinated alkanes (SFA's) used in the present invention are composed of at least one non-fluorinated hydrocarbon segment and at least one perfluorinated hydrocarbon segment. Particularly useful are SFA's which have one non-fluorinated hydrocarbon segment attached to one perfluorinated hydrocarbon segment, according to the general formula $F(CF_2)_n(CH_2)_mH$, or two perfluorinated hydrocarbon segments separated by one non-fluorinated hydrocarbon segment, according to the general formula $F(CF_2)_n(CH_2)_m(CF_2)_oF$.

Another nomenclature which is used herein refers to the above-mentioned SFA's having two or three segments as RFRH and RFRHRF, respectively, wherein $R_F$ designates a perfluorated hydrocarbon segment, $R_H$ designates a non-fluorinated segment. Alternatively, the compounds may be referred to as FnHm and FnHmFo, respectively, wherein F means a perfluorated hydrocarbon segment, H means a non-fluorinated segment, and n, m and o is the number of carbon atoms of the respective segment. For example, F3H3 is used for perfluoropropylpropane. Moreover, this type of nomenclature is usually used for compounds having linear segments. Therefore, unless otherwise indicated, it should be assumed that F3H3 means 1-perfluoropropylpropane, rather than 2-perfluoropropylpropane, 1-perfluoroisopropylpropane or 2-perfluoroisopropylpropane.

Preferably, the semifluorinated alkanes according to the general formulas $F(CF_2)_n(CH_2)_mH$ and $F(CF_2)_n(CH_2)_m(CF_2)_oF$ have segment sizes ranging from 3 to 20 carbon atoms, i.e. n, m and o are independently selected in the range from 3 to 20. SFA's which are useful in the context of the present invention are also described in U.S. Pat. No. 6,262,126, EP-A 965 334, EP-A 965329 and EP-A 2110126, the disclosure of which documents is incorporated herein.

In a further embodiment, the semifluorinated alkane is a compound according to the formula RFRH, whose segments $R_F$ and $R_H$ are linear and each—but independently from one another—have from 3 to 20 carbon atoms. In another particular embodiment, the perfluorinated segment is linear and comprises from 4 to 12 carbon atoms, and/or the non-fluorinated segment is linear and comprises from 4 to 8 carbon atoms. Preferred SFA's include in particular the compounds F4H5, F4H6, F6H4, F6H6, F6H8, and F6H10. Presently most preferred for carrying out the invention are F4H5, F6H6 and F6H8.

Optionally, the composition may comprise more than one SFA. It may be useful to combine SFA's, for example, in order to achieve a particular target property such as a certain density or viscosity. If a mixture of SFA's is used, it is furthermore preferred that the mixture comprises at least one of F4H5, F4H6, F6H4, F6H6, F6H8, and F6H10, and in particular one of F4H5, F6H6 and F6H8. In another embodiment, the mixture comprises at least two members selected from F4H5, F4H6, F6H4, F6H6, F6H8, and F6H10, and in particular at least two members selected from F4H5, F6H6 and F6H8.

Liquid SFA's are chemically and physiologically inert, colourless and stable. Their typical densities range from 1.1 to 1.7 g/cm$^3$, and their surface tension may be as low as 19 mN/m. SFA's of the RFRH type are insoluble in water but also somewhat amphiphilic, with increasing lipophilicity correlating with an increasing size of the non-fluorinated segment.

Liquid SFA's of the RFRH type are being used commercially in ophthalmology, in particular for unfolding an reapplying a retina, for long-term tamponade as vitreous humor substitute (H. Meinert et al., European Journal of Ophthalmology, Vol. 10(3), pp. 189-197, 2000), and as wash-out solutions for residual silicon oil after vitreo-retinal surgery. Experimentally, they have also been used as blood substitutes (H. Meinert et al., Biomaterials, Artificial Cells, and Immobilization Biotechnology, Vol. 21(5), pp. 583-95, 1993). These applications have established SFA's as physiologically well tolerated compounds.

On the other hand, SFA's have not been used as excipients in approved drug products as of today.

It has now surprisingly been found by the inventors that SFA's are not only capable of dissolving propofol at unexpectedly high amounts; the resulting solutions are also very advantageous in other respects. For example, when administered to the skin or to a mucosa, they show an excellent spreading behaviour. At the same time, they do not produce any irritation which is commonly observed when organic solvents are applied to skin or a mucosa. Moreover, as the SFA's provide a lipid-free alternative to the existing formulations such as Diprivan®, they avoid the problem of carrier-mediated hyperlipidaemia.

The solubility of propofol in SFA's is remarkable. With most SFA's including the most preferred ones, i.e. F4H5, F6H6 and F6H8, propofol is freely miscible, in others it exhibits very high solubility. SFA solutions having a propofol concentration of up to 960 mg/mL have been found to be possible. Therefore, the invention also provides highly concentrated liquid preparations of propofol. In order to enable safe and convenient dosing and administration, the composition of the invention should usually have a strength (i.e. concentration of propofol) in the range from about 0.001 wt.-% to about 90 wt.-%. In further embodiments, the propofol concentration is from about 0.01 wt.-% to about 80 wt.-%, or from about 0.1 wt-% to about 50 wt.-%, or from about 1 wt.-% to about 20 wt.-%, or from about 2 wt.-% to about 20 wt.-%, respectively. In further embodiments, the strength is about 1 wt.-% or higher, such as about 2 wt.-%, 5 wt.-%, 10 wt.-%, 20 wt.-%, or 25 wt.-%.

The combined effects of the high solubilisation capacity for propofol, the good spreading behaviour and the lack of irritation on e.g. mucosae also enable the non-injectable administration of propofol for obtaining systemic effects. For example, the composition of the invention may be designed as a concentrated solution (e.g. 2 to 20 wt.-%) for transmucosal (e.g. buccal or sublingual) administration. The high drug concentration in the composition provides a high driving force for the uptake of the active ingredient through the mucosal barrier into the bloodstream. At the same time, the excellent spreading properties ensure the intimate contact of the formulation with the mucosa. Since propofol is a small and lipophilic molecule, it can be expected under these circumstances that it will be rapidly absorbed through a mucosa.

Alternatively, the composition may be administered via the conventional oral route, i.e. by ingestion. Optionally, a liquid-filled hard or soft capsule could be used as a dosage form for this purpose. For a more flexible dosing regimen, a simple oral solution dispensed from a suitable glass or plastic container is also useful.

For most purposes, it will be advantageous to make full use of the high solubilisation capacity of SFA's for propofol and design the composition as a complete solution, i.e. with all or essentially all of the drug substance contained in it being in dissolved form.

Preferably, the composition is in liquid form or in the form of a gel. As used herein, a gel is defined by virtue of its rheological properties. A gel which can be used as a pharmaceutical dosage form is semisolid: it behaves like a solid upon the exertion of low shear force, but above a certain force threshold, the so-called "yield point", it behaves like a viscous fluid. Depending on the desired site and mode of administration, it may be useful to design the composition of the invention as a gel rather than as a liquid solution, for example in order to achieve a longer retention at a topical site of administration. On the other hand, the liquid form is particularly advantageous if the composition is used as a fill material for a sublingual capsule, as an oromucosal or nasal spray, or as an inhalable aerosol.

In order to convert the composition into a gel, a suitable gel-forming excipient or mixture of excipients may be added. Such excipient may be a solid material that is miscible with the SFA or SFA's in which the drug substance is dissolved, such as a solid SFA, or it may be a material which dissolves colloidally within the SFA's and forms a three-dimensional network of associated molecules which give rise to the semisolid behaviour. Examples of excipients capable of gelation in water-free systems include colloidal silicon dioxide (fumed silica) such as Aerosil® 200, certain triterpenes (as taught e.g. in DE 10 2004 030 044 A1), N-stearoyl-L-alanine methyl ester, sorbitan monostearate, and lipophilic cellulose derivatives such as ethylcellulose.

Whether in the form of a liquid or a gel, the composition may comprise further pharmaceutical excipients as needed. For example, it may incorporate a further organic solvent which is physiologically acceptable, such as ethanol, acetone, ethyl acetate, isopropyl alcohol, glycerol, propylene glycol, polyethylene glycol, liquid paraffin, a triglyceride oil, hydrofluorocarbons such as HFA 134a and/or HFA 227, liquid mono- or diglycerides or the like. Depending on which SFA or SFA's have been selected, the solubility of such solvents may be limited, which may restrict the amount to which the solvent can be incorporated. The presence of such solvents may be useful in order to modify the properties of the composition, e.g. the density, viscosity, surface tension or vapour pressure. It may also be useful in order to better solubilise another excipient that is also required in the composition, if this excipient does not dissolve readily in the selected SFA.

If the composition is intended to be administered in aerosolised form, such as an intraoral, nasal or pulmonary aerosol, it may be useful to incorporate a propellant such as HFA 134a and/or HFA 227.

Depending on the particular use which is intended, it may or may not be advisable to add a hydrophilic organic solvent in order to also incorporate some minor amounts of water. In one of the preferred embodiments, the composition of the invention is essentially free of water.

Optionally, the composition may comprise a surfactant. The incorporation of a surfactant may be useful in order to increase the interaction of the formulation with aqueous liquids, such as with the mucus of the oral or nasal mucosa, and it may further improve the spreading of the composition, in particular in wet body surfaces. Optionally, more than one surfactant may be used. Suitable surfactants may be selected from nonionic, anionic, cationic, and zwitterionic surfactants which are physiologically acceptable in view of the intended route of administration. Examples of potentially useful surfactants include native and purified lecithins, semisynthetic phospholipids, poloxamers, pegylated glycerides, Cremophor® EL, Cremophor® RH 40, Cremophor® RH 60, d-α-tocopherol polyethylene glycol 1000 succinate, polysorbate 20, polysorbate 80, Solutol® HS 15, sorbitan monooleate, Labrafil® M-1944CS, Labrafil® M-2125CS, Labrasol®, Gellucire® 44/14, Softigen® 767, and mono- and di-fatty acid esters of PEG 300, 400, or 1750.

Moreover, the composition may incorporate an antioxidant, optionally in combination with a synergist, for example if one of the excipients in the formulation is prone to oxidative degradation. Examples of potentially suitable antioxidants and synergists include vitamin E or vitamin E derivatives, such as Vitamin E-TPGS, Lycopene and its derivatives, gallic acid esters, butyl hydroxyanisole, and butyl hydroxytoluene.

Further pharmaceutical excipients which may be added as needed include colouring agents, flavours, taste-masking agents, sweeteners, bioadhesive agents, viscosity modifiers, stabilisers, preservatives and the like. Examples of suitable lipid-soluble flavours include essential oils such as peppermint oil and eucalyptus oil, camphor, and menthol. Example of useful preservatives include sorbic acid, methyl-, propyl-, butyl- and benzyl parabene, benzoic acid, benzyl alcohol, chlorobutanol, phenol, phenoxyethanol, chlorocresol and metacresol. In a preferred embodiment, the composition is, however, substantially free of lipids such as triglycerides or phospholipids in order to avoid lipid-related toxicities like hyperlipidaemia.

On the other hand, and in contrast to the presently known propofol formulations, the compositions of the invention will often not require the incorporation of a preservative, as they are preferably water-free preparations. Accordingly, a further embodiment of the invention is a water-free, preservative-free composition comprising propofol and at least one SFA. Since preservatives are often associated with the risk of adverse reactions, such as hypersensitivity, it is a considerable advantage of the present invention to be able to provide preservative-free compositions which are not prone to microbial contamination.

In a further particular embodiment, the composition of the invention is sterile. Sterility may be achieved by sterilising the formulation after filling it into an appropriate primary packaging means, e.g. by autoclaving or gamma-sterilisation.

Alternatively, the composition may be sterile filtered and then aseptically filled into sterile primary packages like glass or plastic vials and sealed.

In a further aspect, the invention is also directed to dosage forms comprising a composition as described herein. Dosage forms are understood as types of pharmaceutical compositions or drug products which are suitable for administration. For example, dosage forms of interest which may comprise the composition are soft gelatin capsules, (intra)oral sprays, (intra)oral liquids, (intra)oral gels, nasal sprays, metered-dose inhalers, nebuliser solutions, ear drops, rectal enema and the like.

A preferred type of soft gelatin capsule is designed for oral or intraoral administration. Like most conventional capsule formulations, it may simply be used for being swallowed. For intraoral administration, the capsule shell may be adapted for being easily ruptured by chewing, so that the liquid or gel-like composition is released into the oral cavity. Due to the properties of propofol and its high concentration in the composition, the drug may thus be absorbed into the bloodstream through the oral mucosa, e.g. the sublingual, gingival or buccal mucosa. A particular advantage of the soft gelatin capsule with a liquid or semisolid fill for intraoral administration is that it combines the typical advantages of solid dosage forms (precise dosing, convenience in handling and administration, high stability and long shelf life) with the capability for oromucosal absorption which leads to a rapid onset of the pharmacological effect, without any possibility for a bioavailability-limiting first-pass effect.

Alternatively, if the composition is administered in other intraoral dosage forms such as intraoral liquids or sprays, the advantage of such embodiments is that it is particularly easy to apply flexible dosing schemes. For example, the dose may be easily adjusted to take the desired pharmacological effect (e.g. whether sedation, anaesthesia, or control of migraine headache), the type of patient (ill or healthy, adult or paediatric) into account. Moreover, the administration of an intraoral liquid or spray for oromucosal uptake allows for a dosing-to-effect type of treatment in which consecutive doses are administered until the desired effect is observed in the patient.

In a further embodiment, the composition is used for nasal administration. According to this use, the composition may be presented as a nasal spray or in the form of a nebulised aerosol whose droplet size distribution and fluid dynamics are adapted to achieve a high degree of aerosol deposition on the nasal mucosa. From the nasal mucosa, the absorption of small, lipophilic molecules into the bloodstream is possible, and the composition of the invention is highly suitable for enabling this route of administration as it comprises the drug substance in a high concentration, but also in a well-tolerated carrier. Moreover, it has been found that the composition of the invention can be easily atomised using a conventional nasal spray bottle with atomiser head, generating droplets of about 0.1 to 10 µm in diameter.

In fact, the embodiment according to which the composition is packaged and presented as a spray bottle with an atomiser has the additional advantage that it could be used both for intraoral and for nasal administration.

As mentioned, the composition may also be administered into the lungs by inhalation, using e.g. a metered-dose inhaler or a nebuliser. This is possible as SFA's are highly biocompatible and physiologically inert even when inhaled.

Preferably, the compositions and dosage forms provided by the present invention are used as medicines for all patients who can benefit from receiving propofol. In particular, the medical uses for the induction or maintenance of anaesthesia or sedation, the prevention or treatment of headaches such as migraine headache, the prevention or treatment of nausea, such as chemotherapy-induced nausea, the protection of central nervous tissue (neuroprotection) in brain trauma or injury, and the control of anxiety are proposed as particularly advantageous.

Moreover, the compositions and dosage forms may also be used as veterinary medicaments, both for livestock and companion animals. In particular, the use for initiating and/or maintaining anaesthesia and sedation and controlling anxiety is proposed.

The following examples serve to illustrate the invention; however, these are not to be understood as restricting the scope of the invention.

EXAMPLES

Example 1

Under aseptic conditions, 1 mg ($5.6*10^{-3}$ mmol) of propofol is added under stirring to 100 mL of perfluorobutylpentane (F4H5) to form a clear solution. After further 15 minutes of stirring, the solution is sterile filtered and filled into sterile brown glass vials, which are subsequently sealed.

Example 2

Under aseptic conditions, 1 mg ($5.6*10^{-3}$ mmol) of propofol is added under stirring to 1 mL of perfluorobutylpentane (F4H5) to form a clear solution. After further 15 minutes of stirring, the solution is sterile filtered and filled into a sterile brown glass vial, which is subsequently sealed.

Example 3

Under aseptic conditions, 100 mg (0.56 mmol) of propofol is added under stirring to 1 mL of perfluorobutylpentane (F4H5) to form a clear solution. After further 15 minutes of stirring, the solution is sterile filtered and filled into a sterile brown glass vial, which is subsequently sealed.

Example 4

Under aseptic conditions, 1 g (5.6 mmol) of propofol is added under stirring to 1 mL of perfluorobutylpentane (F4H5) to form a clear solution. After further 15 minutes of stirring, the solution is sterile filtered and filled into a sterile brown glass vial, which is subsequently sealed.

Example 5

Under aseptic conditions, 100 mg (0.56 mmol) of propofol is added under stirring to 1 mL of perfluorohexyloctane (F6H8) to form a clear solution. After further 15 minutes of stirring, the solution is sterile filtered and filled into a sterile brown glass vial, which is subsequently sealed.

Example 6

Under aseptic conditions, 100 mg (0.56 mmol) of propofol is added under stirring to 0.5 mL of perfluorohexyloctane (F6H8) and 0.5 mL of perfluorobutylpentane (F4H5) to form a clear solution. After further 15 minutes of stirring, the solution is sterile filtered and filled into a sterile brown glass vial, which is subsequently sealed.

Example 7

Under aseptic conditions, 1 g (5.6 mmol) of propofol is added under stirring to 1 mL of perfluorohexyloctane (F6H8)

to form a clear solution. After further 15 minutes of stirring, the solution is sterile filtered and filled into a sterile brown glass vial, which is subsequently sealed.

Example 8

Under aseptic conditions, 100 mg (0.56 mmol) of propofol and 2 mg (4.6*10$^{-3}$ mmol) α-tocopherol are added under stirring to 1 mL of perfluorobutylpentane (F4H5) to form a clear solution. After further 15 minutes of stirring, the solution is sterile filtered and filled into a sterile brown glass vial, which is subsequently sealed.

Example 9

Under aseptic conditions, 100 mg (0.56 mmol) of propofol and 30 mg (7*10$^{-2}$ mmol) of α-tocopherol are added under stirring to 1 mL of perfluorohexyloctane (F6H8) to form a clear solution. After further 15 minutes of stirring, the solution is sterile filtered and filled into a sterile brown glass vial, which is subsequently sealed.

Example 10

Under aseptic conditions, 100 mg (0.56 mmol) of propofol and 10 mg (6.6*10$^{-2}$ mmol) of camphor are added under stirring to 1 mL of perfluorobutylpentane (F4H5) to form a clear solution. After further 15 minutes of stirring, the solution is sterile filtered and filled into a sterile brown glass vial, which is subsequently sealed.

Example 11

Under aseptic conditions, 100 mg (0.56 mmol) of propofol and 100 mg (2.2 mmol) of ethanol are added under stirring to 1 mL of perfluorobutylpentane (F4H5) to form a clear solution. After further 15 minutes of stirring, the solution is sterile filtered and filled into a sterile brown glass vial, which is subsequently sealed.

Example 12

Under aseptic conditions, 100 mg (0.56 mmol) of propofol and 100 mg (2.2 mmol) of ethanol are added under stirring to 1 mL of perfluorohexylhexane (F6H6) to form a clear solution. After further 15 minutes of stirring, the solution is sterile filtered and filled into a sterile brown glass vial, which is subsequently sealed.

Example 13

In analogy to example 1, two solutions of propofol having a nominal propofol content of 400 mg/g were prepared. As solvent, the first solution comprised perfluorobutylpentane (F4H5), while the second solution comprised perfluorohexyloctane (F6H8). No further ingredients were used. For testing their stability, sample vials of the respective solutions were stored at 25° C./60% RH, 30° C./65% RH, and 40° C./75% RH, respectively. After one and after three months of storage, samples were analysed by GC/MS according to Ph.Eur.2.2.2. In result, the propofol content in all samples was well above 95% of the nominal value, and also far above 95% of the actual content measured immediately after the preparation of the solutions, thus indicating a good stability of the formulations. Table 1 shows the results in detail. The percentages shown are relative to the nominal propofol content.

TABLE 1

| | F4H5 | | | F6H8 | | |
|---|---|---|---|---|---|---|
| | 25° C./ 60% | 30° C./ 65% | 40° C./ 75% | 25° C./ 60% | 30° C./ 65% | 40° C./ 75% |
| Start (t = 0) | 106.2% | 106.2% | 106.2% | 99.2% | 99.2% | 99.2% |
| 1 month | 105.4% | 105.4% | 105.2% | 98.7% | 98.7% | 98.3% |
| 3 months | 105.3% | 105.1% | 105.0% | 98.3% | 98.3% | 98.1% |

Example 14

In analogy to example 13, two solutions of propofol having a nominal propofol content of 300 mg/g were prepared, alternatively using perfluorobutylpentane (F4H5) or perfluorohexyloctane (F6H8) as sole excipients. Of each formulation, an amount representing 100 mg propofol per kg body weight was administered buccally to three anaesthetised Wistar arts. In detail, Wistar rats (n=3; for each group) weighing 348±24 g were randomized to the experimental groups. The animals were pre-oxygenated and anaesthetised with ketamine (Ketanest® 10%, Pfizer, Karlsruhe, Germany) and xylazine (Rompun®, BayerVital, Leverkusen, Germany). Vascular catheters (Portex, Smiths medical, Kent, UK) were placed in the femoral artery and vein. Anaesthetised animals were placed in supine position, the anterior neck was dissected and a tracheotomy was performed. To avoid gastric or enteral displacement of the test compounds a ligation of the proximal oesophagus followed. Arterial blood pressure was monitored by attaching the vascular catheters to standard pressure transducers. Heart rate was monitored by electrocardiogram (ECG). Body temperature was monitored continuously using a rectal probe, and normothermia was maintained with electric warming pads. Anaesthesia was maintained with continuous intravenous infusions of ketamine and xylazine until the completion of the experiment. Arterial pressure and ECG were monitored and acquired by a calibrated special multiple-channel online recorder (MedIS, Medical Device Integration System, Hochschule Mannheim, Germany). Animals were ventilated with a Fabian Plus® neonatal respirator (Acutronic Medical Systems AG, Hirzel, Switzerland) using a pressure control mode (IPPV) with a FiO$_2$ of 0.5, a tidal volume of 6 ml/kg, a positive end expiratory pressure of 3 cm H$_2$O and a respiratory rate of 70-80 min$^{-1}$.

Baseline blood samples (0.2 µl) were collected prior to the buccal placement of the test compounds (baseline values). F4H5- and F6H8-based propofol formulations were administered as boluses into the buccal pouch of the animals, using a laboratory pipette. Each animal received 100 mg/kg body weight of the respective solution. In average, every animal received 34±2 mg of propofol. Blood samples (0.2 µl) were collected at 5, 10, 15, 30, 60, 90 and 120 minutes after buccal application of the test compounds. The samples were centrifuged and stored at −20° C. until analysis. The determination of propofol concentrations was performed with mass spectrometry (MS) and high performance liquid chromatography (HPLC).

In result, haemodynamic monitoring provided evidence that the formulations were well tolerated. No changes in heart frequency and arterial blood pressure were observed.

The systemic uptake of propofol was indicated by mean plasma levels rising above 100 ng/ml after 10 minutes in the case of the F4H5-based formulation and 15 minutes in the case of the F6H8-based formulation. Within the sampling time, maximum plasma levels of 334 ng/ml were observed by the F4H5-based formulation after 120 minutes, and of 259 ng/ml after 60 minutes in the case of the F6H8-based formulation. However, at least for the F4H5-based formulation it appeared that the actual maximum plasma levels were not yet reached at the end of the experiment. The concentrations for all sampling times are given in table 2. Generally speaking, such propofol concentrations are slightly lower than those typically observed in general anaesthesia using propofol, but are nevertheless believed to be effective for sedation, e.g. in the context of intensive care.

TABLE 2

|  | F4H5 | | F6H8 | |
| --- | --- | --- | --- | --- |
| min | $C_{av}$ (ng/ml) | SD (ng/ml) | $C_{av}$ (ng/ml) | SD (ng/ml) |
| Start (t = 0) | 0.0 | n/a | 0.0 | n/a |
| 5 | 0.0 | n/a | 0.0 | n/a |
| 10 | 108.5 | 72.4 | 0.0 | n/a |
| 15 | 147.8 | 92.8 | 120.6 | 14.7 |
| 30 | 215.2 | 35.9 | 218.1 | n/a |
| 45 | 180.8 | 53.4 | 219.7 | 115.7 |
| 60 | 262.2 | 108.0 | 259.4 | 137.3 |
| 90 | 266.8 | 51.8 | 182.7 | 51.3 |
| 120 | 334.3 | 29.3 | 213.1 | 5.0 |

$C_{av}$: Mean propofol plasma concentrations (n = 3)
SD: Standard deviation

The invention claimed is:

1. A pharmaceutical composition comprising a therapeutically effective amount of propofol and a semifluorinated alkane.

2. The composition of claim 1, wherein the semifluorinated alkane is a compound of formula

RFRH or of formula

RFRHRF wherein RF is a perfluorinated hydrocarbon segment with 20 or less carbon atoms, and
wherein RH is a non-fluorinated hydrocarbon segment with 3 to 20 carbon atoms.

3. The composition of claim 1, wherein the semifluorinated alkane is a compound of formula $F(CF_2)_n(CH_2)_mH$ or of formula $F(CF_2)_n(CH_2)_m(CF_2)_oF$ wherein n, m and o are independently selected in the range from 3 to 20.

4. The composition of claim 3, wherein the semifluorinated alkane is a compound of formula $F(CF_2)_n(CH_2)_m$ wherein n and m are independently selected in the range of 3 to 10.

5. The composition of claim 4, wherein the semifluorinated alkane is selected from $(CF_2)_4(CH_2)_5H$, $F(CF_2)_6(CH_2)_6H$ and $F(CF_2)_6(CH))$.

6. The composition of claim 1, wherein the concentration of propofol is about 1 wt.-% or higher.

7. The composition of claim 1, wherein essentially all of the propofol comprised therein is in dissolved form.

8. The composition of claim 1, being in the form of a liquid or a gel.

9. The composition of claim 1, being substantially free of lipids such as trigylcerides or phospholipids.

10. A pharmaceutical dosage form comprising the composition of claim 1.

11. The dosage form of claim 10, being selected from a soft capsule or an oral spray, a nasal spray, an inhalable aerosol, an oral gel, and an oral liquid.

12. A pharmaceutical kit comprising a container and therein the composition of claim 1, wherein the container comprises a means for atomising the composition.

13. A method of treatment comprising a step of administering of the composition of claim 1 as a medicine to a patient, wherein the medicine is for inducing or maintaining anaesthesia or sedation, for neuroprotection in brain injury, for the treatment of headache or nausea, or for controlling anxiety.

14. A method of treatment according to claim 13, wherein the medicine is administered orally, oromucosally or nasally.

15. A method of treatment comprising a step of administering the composition of claim 1 as a veterinary medicament to livestock or to a companion animal wherein the medicament is for initiating and/or maintaining anaesthesia and sedation or for controlling anxiety.

16. A method of treatment comprising a step of administering the dosage form of claim 10 as a medicine to a patient, wherein the medicine is for inducing or maintaining anaesthesia or sedation, for neuroprotection in brain injury, for the treatment of headache or nausea, or for controlling anxiety.

17. A method of treatment comprising a step of administering the dosage form of claim 10 as a veterinary medicament to livestock or to a companion animal, wherein the medicament is for initiating and/or maintaining anaesthesia and sedation or for controlling anxiety.

* * * * *

UNITED STATES PATENT AND TRADEMARK OFFICE
CERTIFICATE OF CORRECTION

PATENT NO. : 8,796,340 B2
APPLICATION NO. : 13/511184
DATED : August 5, 2014
INVENTOR(S) : Bastian Theisinger and Sonja Theisinger It is certified that error appears in the above-identified patent and that said Letters Patent is hereby corrected as shown below:

IN THE CLAIMS:

Column 12, line 4, the formula reading "$F(CF_2)_n(CH_2)_m$" should read -- $F(CF_2)_n(CH_2)_mH$ --.

Column 12, lines 9-10, the formulas reading "$(CF_2)_4(CH_2)_5H, F(CF_2)_6(CH_2)_6H$ and $F(CF_2)_6(CH)$)" should read -- $F(CF_2)_4(CH_2)_5H, F(CF_2)_6(CH_2)_6H$ and $F(CF_2)_6(CH_2)_8H$ --.

Signed and Sealed this
Ninth Day of December, 2014

Michelle K. Lee
*Deputy Director of the United States Patent and Trademark Office*